(12) United States Patent
Gibanel et al.

(10) Patent No.: US 10,526,277 B2
(45) Date of Patent: Jan. 7, 2020

(54) FOOD OR BEVERAGE CONTAINERS COATED WITH POLYMERS OF DI(AMIDO(ALKYL)PHENOL) COMPOUNDS

(71) Applicant: SWIMC LLC, Cleveland, OH (US)

(72) Inventors: Sebastien Gibanel, Givry (FR); Benoit Prouvost, Abergement de Cuisery (FR); Bernard Boutevin, Montpellier (FR)

(73) Assignee: SWIMC LLC, Cleveland, OH (US)

( * ) Notice: Subject to any disclaimer, the term of this patent is extended or adjusted under 35 U.S.C. 154(b) by 507 days.

(21) Appl. No.: 15/029,439

(22) PCT Filed: Oct. 16, 2014

(86) PCT No.: PCT/US2014/060845
§ 371 (c)(1),
(2) Date: Apr. 14, 2016

(87) PCT Pub. No.: WO2015/057932
PCT Pub. Date: Apr. 23, 2015

(65) Prior Publication Data
US 2016/0272576 A1    Sep. 22, 2016

Related U.S. Application Data

(60) Provisional application No. 61/892,001, filed on Oct. 17, 2013.

(51) Int. Cl.
*B32B 15/08* (2006.01)
*C07C 235/34* (2006.01)
(Continued)

(52) U.S. Cl.
CPC ............ *C07C 235/34* (2013.01); *B65D 85/72* (2013.01); *C07C 231/02* (2013.01);
(Continued)

(58) Field of Classification Search
CPC ........................... C07C 235/34; C07C 231/02
See application file for complete search history.

(56) References Cited

U.S. PATENT DOCUMENTS 2,633,458 A   3/1953  Shokal
3,498,952 A   3/1970  Wiener
(Continued)

FOREIGN PATENT DOCUMENTS

CA    2235077 A1    4/1997
EP    0 404 039 A1  12/1990
(Continued)

OTHER PUBLICATIONS

Extended European Search Report for Application No. 15796095.6, dated Nov. 7, 2017, 8 pages.
(Continued)

*Primary Examiner* — Prashant J Khatri
*Assistant Examiner* — Zachary M Davis
(74) *Attorney, Agent, or Firm* — Patterson Thuente Pedersen, P.A.

(57) ABSTRACT

Di(amido(alkyl)phenol) compounds and upgraded molecular weight polymers made from such compounds have particular utility in coating compositions, especially for use on food and beverage contact substrates that are formed into or will be formed into containers or container components.

22 Claims, 3 Drawing Sheets

(51) Int. Cl.
| | |
|---|---|
| *B65D 85/72* | (2006.01) |
| *C07C 231/02* | (2006.01) |
| *C08G 63/685* | (2006.01) |
| *C08G 64/16* | (2006.01) |
| *C08G 65/40* | (2006.01) |
| *C08G 71/04* | (2006.01) |
| *C09D 167/00* | (2006.01) |
| *C09D 169/00* | (2006.01) |
| *C09D 171/00* | (2006.01) |
| *C09D 175/12* | (2006.01) |

(52) U.S. Cl.
CPC ....... *C08G 63/685* (2013.01); *C08G 64/1641* (2013.01); *C08G 65/40* (2013.01); *C08G 71/04* (2013.01); *C09D 167/00* (2013.01); *C09D 169/00* (2013.01); *C09D 171/00* (2013.01); *C09D 175/12* (2013.01)

(56) References Cited

U.S. PATENT DOCUMENTS

| | | |
|---|---|---|
| 3,943,187 A | 3/1976 | Wu |
| 4,076,676 A | 2/1978 | Sommerfeld |
| 4,145,333 A | 3/1979 | Minagawa et al. |
| 4,212,781 A | 7/1980 | Evans et al. |
| 4,246,198 A | 1/1981 | Rosenberger et al. |
| 4,247,439 A | 1/1981 | Matthews et al. |
| 4,285,847 A | 8/1981 | Ting |
| 4,410,681 A | 10/1983 | Prindle |
| 4,413,015 A | 11/1983 | Anderson et al. |
| 4,446,258 A | 5/1984 | Chu et al. |
| 4,517,322 A | 5/1985 | Birkmeyer et al. |
| 4,577,042 A | 3/1986 | Collins et al. |
| 4,963,602 A | 10/1990 | Patel |
| 5,134,218 A * | 7/1992 | Brennan ............. C08G 59/063 528/104 |
| 5,296,525 A | 3/1994 | Spencer |
| 5,527,840 A | 6/1996 | Chutko et al. |
| 5,717,054 A | 2/1998 | Schultz |
| 5,830,952 A | 11/1998 | Pedersen et al. |
| 5,922,817 A | 7/1999 | Pedersen et al. |
| 6,465,601 B1 | 10/2002 | Wiesendanger et al. |
| 6,974,631 B2 | 12/2005 | Hayes et al. |
| 7,189,787 B2 | 3/2007 | O'Brien et al. |
| 7,381,472 B2 | 6/2008 | Brandenburger et al. |
| 7,910,170 B2 | 3/2011 | Evans et al. |
| 8,092,876 B2 | 1/2012 | O'Brien et al. |
| 8,129,495 B2 | 3/2012 | Evans et al. |
| 8,202,960 B1 | 6/2012 | Morizur et al. |
| 8,207,287 B1 | 6/2012 | Morizur et al. |
| 8,530,570 B2 | 9/2013 | Mijolovic et al. |
| 9,540,484 B2 | 1/2017 | Craun et al. |
| 9,605,177 B2 | 3/2017 | Tang et al. |
| 2001/0051227 A1 * | 12/2001 | Jung ...................... B05D 1/265 427/486 |
| 2005/0196629 A1 | 9/2005 | Bariatinsky et al. |
| 2006/0073294 A1 * | 4/2006 | Hutchinson ............. B29C 44/04 428/35.7 |
| 2006/0182974 A1 | 8/2006 | Garnault et al. |
| 2010/0068433 A1 | 3/2010 | Gibanel et al. |
| 2010/0256322 A1 | 10/2010 | Kramer et al. |
| 2011/0178239 A1 | 7/2011 | Mijolovic et al. |
| 2011/0315591 A1 | 12/2011 | Lespinasse et al. |
| 2012/0149863 A1 | 6/2012 | Morizur |
| 2012/0301646 A1 * | 11/2012 | List .................... C08G 59/1422 428/35.7 |
| 2013/0052381 A1 | 2/2013 | Gallucci et al. |
| 2013/0172421 A1 | 7/2013 | Zheng et al. |
| 2013/0206756 A1 | 8/2013 | Niederst et al. |
| 2013/0280455 A1 | 10/2013 | Evans et al. |
| 2013/0316109 A1 | 11/2013 | Niederst et al. |
| 2014/0322465 A1 | 10/2014 | Kaleem et al. |
| 2016/0024337 A1 | 1/2016 | Bode et al. |
| 2016/0032048 A1 | 2/2016 | Craun et al. |
| 2016/0107818 A1 | 4/2016 | Kaleem et al. |
| 2016/0122581 A1 | 5/2016 | You et al. |

FOREIGN PATENT DOCUMENTS

| | | |
|---|---|---|
| JP | S50-151222 A | 12/1975 |
| JP | 2002-307604 | 10/2002 |
| WO | WO-2006/045017 A1 | 4/2006 |
| WO | WO-2007/048094 A2 | 4/2007 |
| WO | WO-2007/064608 A1 | 6/2007 |
| WO | WO 2010/075395 A2 | 7/2010 |
| WO | WO-2011130671 A2 | 10/2011 |
| WO | WO 2012/064483 A1 | 5/2012 |
| WO | WO 2012/064484 A1 | 5/2012 |
| WO | WO-2012109278 A2 | 8/2012 |
| WO | WO-2012/161758 A2 | 11/2012 |
| WO | WO-2013090702 A2 | 6/2013 |
| WO | WO 2013/119686 A1 | 8/2013 |
| WO | WO-2013149234 A2 | 10/2013 |
| WO | WO 2014/025407 A1 | 2/2014 |
| WO | WO-2014025411 A1 | 2/2014 |
| WO | WO-2014025997 A1 | 2/2014 |
| WO | WO-2014072216 A1 | 5/2014 |
| WO | WO 2014/140232 A2 | 9/2014 |
| WO | WO 2014/140233 A1 | 9/2014 |
| WO | WO 2014/140234 A1 | 9/2014 |
| WO | WO-2015183892 A1 | 12/2015 |
| WO | WO-2016201407 A1 | 12/2016 |

OTHER PUBLICATIONS

Hu, et al., "Synthesis and Characterization of Thermosetting Furan-Based Epoxy Systems," Macromolecules, May 9, 2014, vol. 47, pp. 3332-3342.

International Search Report and Written Opinion for Application No. PCT/US2015/027466, dated Aug. 10, 2015, 11 pages.

International Preliminary Report on Patentability for Application No. PCT/US2014/060845, dated Apr. 28, 2016, 10 pages.

International Preliminary Report on Patentability for Application No. PCT/US2015/027466, dated Dec. 1, 2016, 10 pages.

"Potentially safer, greener alternative to BPA could come from papermaking waste," American Chemical Society News Release, Mar. 2014, 5 pages.

Stove E., "BPA substitute made from paper industry leftovers," chemistry world, Mar. 17, 2014, 1 page.

Benyahya, Sofia et al. "Synthesis of glycerin carbonate-based intermediates using thiol-ene chemistry and isocyanate free polyhydroxyurethanes therefrom", Polym. Chem., 2, pp. 2661-2667 (2011).

Agag, Tarek et al., "Benzoxazole Resin: A Novel Class of Thermoset Polymer via Smart Benzoxazine Resin", Macromolecules, 45, pp. 8991-8997 (2012).

Liew, Lydia P.P. et al., "Discovery and preliminary structure-activity relationship analysis of 1,14-sperminediphenylacetamides as potent and selective antimalarial lead compounds", Bioorganic & Medicinal Chemistry Letters, 23, pp. 452-454 (2013).

Dytek® 2-Methylpentamethylenediamine (MPMD) (Dytek® A amine), Technical Information Sheet, 1 page (Mar. 15, 2012).

Behbehani, Haider et al., "Efficient atom economic approaches towards macrocyclic crown diamides via ring-closing metathesis", Tetrahedron Letters, 43, pp. 6421-6426 (2002).

Erichsen, Bend and Impact Tester Model 471, Technical Description and Operating Instructions, 2 pages (2007).

Raines, Daniel J. et al., "Interactions of a Periplasmic Binding Protein with a Tetradentate Siderophore Mimic", Angewandte Chemie Int. Ed., 52, pp. 4595-4598 (2013).

Croda, Priamine™ 1071-Bridging flexibility and hardness of epoxy systems for marine and protective coatings, Croda Coatings & Polymers, 4 sheets (2011).

"The Jeffamine® Polyetherimines", Technical Data Sheet, Huntsman, 6 pages (2007).

"Outline of Nylon-MXD6", Mitsubishi Gas Chemical Co., Inc., 2 pages (2007).

(56) References Cited

OTHER PUBLICATIONS

Rosowsky, A. et al., "Structural Analogues of $_L$-Glutamic Acid γ-(4-Hydroxyanilide) and γ-(3,4-Dihydroxyanilide) as Potential Agents against Melanoma", Journal of Medicinal Chemistry, vol. 22, No. 9, pp. 1034-1037 (1979).
Mikroyannidis, John A. et al., "Synthesis and Thermal Behaviour of New High-Temperature Silicon-Containing Bismaleimides", British Polymer Journal, 23, pp. 309-314 (1990).
Abbas, Ashraf A., "Synthesis of Mixed-donor Azaoxathia Macrocyclic Tetraamides, Acyclic Polyether di/and Tetraamides and Their C-Pivot Lariat Derivatives", J. Heterocyclic Chem., 44, pp. 651-661 (2007).
International Search Report and Written Opinion for corresponding International Application No. PCT/US2014/060845.
Polarity of Organic Compounds, Virtual Chembook, pp. 1-4, Charles E. Ophardt, copyright 2003 (the year of publication is sufficiently earlier than the effective U.S. filing date and any foreign priority date so that the particular month of publication is not in issue) downloaded at: http://chemistry.elmhurst.edu/vchembook/213organicfcgp.html.

\* cited by examiner

FOOD OR BEVERAGE CONTAINERS COATED WITH POLYMERS OF DI(AMIDO(ALKYL)PHENOL) COMPOUNDS

CROSS REFERENCE TO RELATED APPLICATIONS

This application is a national stage filing under 35 U.S.C. § 371 of International Application No. PCT/US2014/060845 filed Oct. 16, 2014, which claims priority under 35 U.S.C. § 119 to U.S. Provisional Application No. 61/892,001 filed Oct. 17, 2013, the disclosures of both of which are incorporated herein by reference.

TECHNICAL FIELD

This invention relates to polyphenols and to polymers made from them.

BACKGROUND

Bisphenol A and bisphenol F have been used to prepare polymers having a variety of properties and uses. For example, bisphenol A or bisphenol F may be reacted with phosgene to provide polycarbonates that may be used to form packaging containers, or with epichlorohydrin to provide packaging coatings. There is a desire to reduce or eliminate the use of certain bisphenol A-based and bisphenol F-based compounds in containers and coatings, and especially those involving contact with foods or beverages.

SUMMARY

Phenol-terminated diamides may be made by direct amination or transamination, for example by reacting (viz., by combining reactants comprising) a phenolic acid or ester (e.g., a phenolic monoacid or monoester) and a diamine (e.g., a linear aliphatic primary diamine) to produce a polyphenol of Formula I shown below:

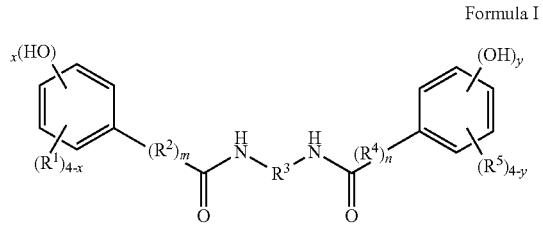

Formula I wherein:
x and y may be the same or different, are each an integer from 1 to 3, and may designate hydroxyl groups located at ortho-, meta- or preferably para-positions with respect to the $R^2$ or $R^4$ group on the indicated aromatic ring;
m and n may be the same or different, preferably are the same, and are 0 or 1;
$R^1$ and $R^5$ may be the same or different and independently are monovalent atoms (for example, hydrogen, or a heteroatom such as a halogen) or monovalent groups (e.g., C, O, N, S, or P containing-groups), typically organic groups (for example, aliphatic or cycloaliphatic groups that may be linear or branched, of aromatic groups) which may contain heteroatoms (for example, O, N or S atoms), with $R^1$ and $R^5$ preferably being hydrogen;
$R^2$ and $R^4$ may be the same or different, preferably are the same, and when present independently may be divalent aliphatic, cycloaliphatic or aromatic organic groups (for example, a —$CH_2$—, —$CH_2CH_2$—, —$C_6H_{10}$— or —$C_6H_4$—$C_6H_4$-radical) that may be linear or branched, may contain heteroatoms, and preferably contain from 1 to about 12 carbon atoms;
$R^3$ is a divalent organic group (for example, an aliphatic or cycloaliphatic group that may be linear or branched, or an aromatic group), may contain heteroatoms (for example, O, N or S atoms), and preferably contains from 1 to about 200 and more preferably from 2 to about 150 or about 2 to 50 carbon atoms.

When m in Formula I is 0, the Formula I polyphenol could be described as a C—C' hydroxybenzene diamide. When m in Formula I is 1 or more, the Formula I polyphenol could be described as a C—C' hydroxybenzyl diamide. For brevity, the term di(amido(alkyl)phenol) will be used to refer collectively to both classes of compounds, viz., compounds where m is either 0 or is 1 or more.

The disclosed di(amido(alkyl)phenol) compounds may also be made by reacting (viz., by combining reactants comprising) a phenolic amine (e.g., a phenolic primary monoamine) and a diacid (e.g., a linear aliphatic diacid) or a diester (e.g., a linear aliphatic diester) to produce a polyphenol of Formula II shown below:

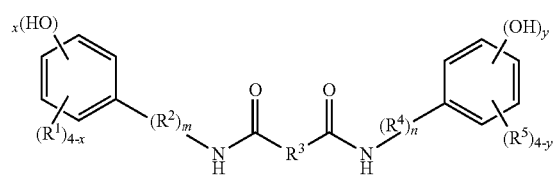

Formula II wherein x, y, m, n and $R^1$ through $R^5$ are as defined above.

By analogy with the nomenclature used for Formula I, when m in Formula II is 0, the Formula II polyphenol could be described as an N—N' hydroxybenzene diamide, and when m is 1 or more, the Formula II polyphenol could be described as an N—N' hydroxybenzyl diamide. For brevity, the term di(amido(alkyl)phenol) will also be used to refer collectively to both classes of Formula II compounds, viz., compounds where m is either 0 or is 1 or more. The compounds of Formula I and II may also be referred to as α, Ω telechelic diphenols, viz., compounds with reactive phenol groups at each end of the compound backbone or chain.

A preferred class of compounds of Formulas I and II may be collectively depicted as polyphenols of Formula III shown below:

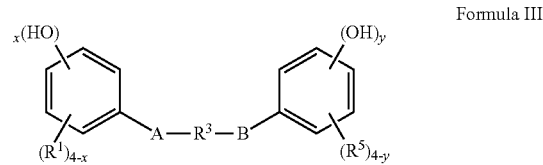

Formula III wherein A and B contain amido groups linked to the $R^3$ group through a nitrogen atom or carbonyl group, and x, y, $R^1$, $R^3$ and $R^5$ are as defined above. In some embodiments, the compounds of Formula III are compounds of Formula I and Formula II in which m and n are the same, and $R^2$ and $R^4$ are the same. In some embodiments, the $R^1$ and $R^5$ groups are hydrogen. In other embodiments, one or more $R^1$ or $R^5$ groups other than hydrogen (e.g., an organic $R^1$ or $R^5$ group described herein) may be located on one or both (and preferably both) depicted phenylene rings. In an embodiment, A and B are the same. In another embodiment, A and B are the same and are arranged in mirror image fashion with respect to $R^3$. In another embodiment, A is —$R^2_m$CONH— and B is —NHCOR$^2_m$— or A is —$R^2_m$NHCO— and B is —CONHR$^2_m$— wherein m and $R^2$ are as defined above.

The compounds of Formulas I and II and polyphenols of Formula III may be made by the reactions described above or by other suitable reactions or processes that lead to the same end products.

Methods for making the compounds of Formulas I and II and polyphenols of Formula III by combining the above-described reactants are also provided. Yields for the chosen reaction may be influenced by a variety of factors including for example steric hindrance of the amine and ester groups, donor or acceptor electronic effects of the substituent groups bearing the amine or ester functions and the position and nature of the substituents on the aromatic rings. The reaction yield may for example be improved by removing the alcohol byproduct, adding heat or employing a suitable catalyst.

The disclosed di(amido(alkyl)phenol) compounds should have reactivity like other phenol compounds (for example, by being reactive toward electrophilic aromatic substitution on activated or stabilized carbon atoms of the aromatic ring, and especially at ring carbon atoms ortho or para to the hydroxyl group). The disclosed di(amido(alkyl)phenol) compounds thus may be combined with a variety of materials that react with hydroxyl groups on the phenol rings to make a variety of homopolymers and copolymers (e.g., linear homopolymers and copolymers) including polyethers, polyesters, vinyl esters, polyurethanes, polyureas, polycarbonates and phenolic resins. The resulting homopolymers and copolymers can offer properties similar in some desirable respects to desirable properties of homopolymers and copolymers derived from bisphenol A or bisphenol F (for example, having enhanced flexibility, adhesion, resistance to hydrolysis or resistance to solvents), while differing from homopolymers and copolymers derived from bisphenol A or bisphenol F in other useful or important respects (for example, having reduced estrogenic activity).

BRIEF DESCRIPTION OF THE DRAWING

In the accompanying Drawing.

DETAILED DESCRIPTION

Figure 1:
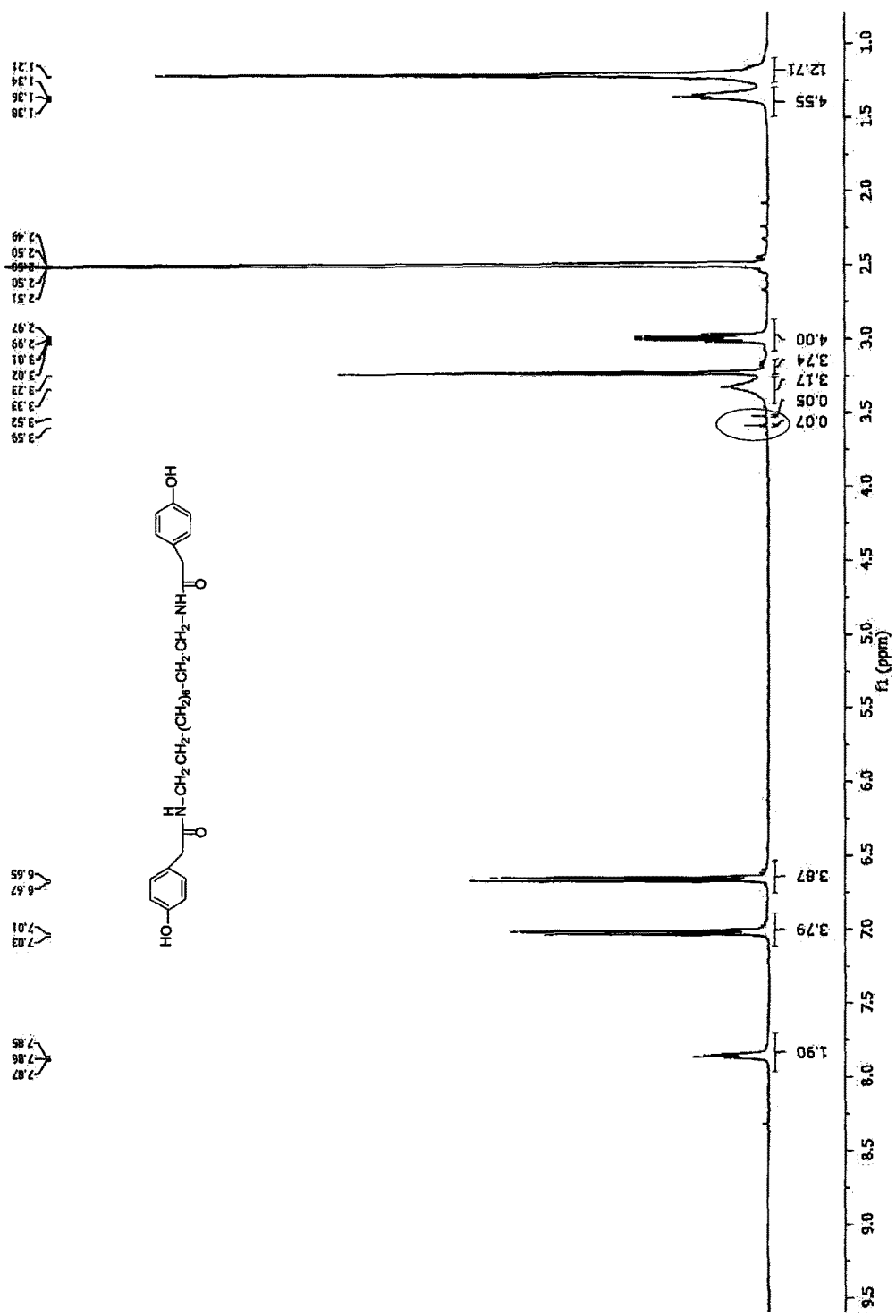
FIG. 1 through FIG. 3 are proton NMR spectra for the di(amido(alkyl)phenol) compounds prepared in Examples 1, 2 and 5.

As used herein, "a," "an," "the," "at least one," and "one or more" are used interchangeably. Thus, for example, a coating composition that contains "a" stabilizer can be interpreted to mean that the coating composition includes "one or more" stabilizers.

The term "bisphenol" refers to a polyhydric polyphenol having two phenylene groups that each include a six-carbon ring and a hydroxyl group attached to a carbon atom of the ring, wherein the rings of the two phenylene groups do not share any atoms in common.

The terms "comprises" and variations thereof do not have a limiting meaning where these terms appear in the description and claims.

The term "crosslinker" refers to a molecule capable of forming a covalent linkage between copolymers (e.g., between polymers) or between two different regions of the same copolymer.

The term "easy open end" refers to a can end (typically an end of a food or beverage container) that includes (i) a frangible opening portion (which for some beverage can ends functions as a drinking spout) and (ii) a riveted portion for attaching a pull tab there for purposes of opening the frangible opening portion to access the product housed within a can or container.

The terms "estrogenic activity" or "estrogenic agonist activity" refer to the ability of a compound to mimic hormone-like activity through interaction with an endogenous estrogen receptor, typically an endogenous human estrogen receptor.

The term "food-contact surface" refers to a surface of an article (e.g., a food or beverage container) that is in contact with, or suitable for contact with, a food or beverage product.

The term "mobile" when used with respect to a compound in a coating composition means that the compound can be extracted from the coating composition when a coating (typically ~1 mg/cm$^2$) is exposed to a test medium for some defined set of conditions, depending on the end use. An example of these testing conditions is exposure of the cured coating to HPLC-grade acetonitrile for 24 hours at 25° C.

The term "on," when used in the context of a coating applied on a surface or substrate, includes both coatings applied directly or indirectly to the surface or substrate. Thus for example, a coating applied to a primer layer overlying a substrate constitutes a coating applied on the substrate.

The term "organic group" means a hydrocarbon group (with optional elements other than carbon and hydrogen, such as oxygen, nitrogen, sulfur, and silicon) that may be further classified as an aliphatic group, cyclic group (e.g., aromatic and cycloaliphatic groups), or combination of aliphatic and cyclic groups (e.g., alkaryl and aralkyl groups). The term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group (e.g., an n-propyl isopropyl group). The term "alkenyl group" means an unsaturated, linear or branched hydrocarbon group with one or more carbon-carbon double bonds (e.g., a vinyl group). The term "cyclic group" means a closed ring hydrocarbon group that is classified as an alicyclic group or an aromatic group, both of which can include heteroatoms. The term "alicyclic group" means a cyclic hydrocarbon group having properties resembling those of aliphatic groups. A group that may be the same as or different from other groups may be referred to as being "independently" something. Substitution on the organic groups of the disclosed polyphenols is contemplated. The terms "group" and "moiety" may be used to differentiate between chemical species that allow for substitution or that may be substituted and those that do not allow or may not be so substituted. The term "group" is intended to be a recitation of both the particular moiety, as well as a recitation of the broader class of substituted and unsubstituted structures that includes the moiety. Thus, when the term "group" is used to describe a chemical substituent, the described chemical material includes the unsubstituted group and that group with O, N, Si, or S atoms, for example, in the chain (as in an alkoxy group) as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, isopropyl, t-butyl, heptyl, dodecyl, octadecyl, amyl, 2-ethylhexyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, isopropyl, t-butyl, heptyl, dodecyl, octadecyl, amyl, 2-ethylhexyl, and the like.

The term "polyphenol" refers to a polyhydric material having two phenylene groups that each include a six-carbon ring and a hydroxyl group attached to a carbon atom of the ring, wherein the rings of the two phenylene groups do not share any atoms in common.

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The term "substantially free" when used with respect to a coating composition that may contain a particular mobile compound means that the coating composition contains less than 1,000 parts per million (ppm) of the recited mobile compound. The term "essentially free" when used with respect to a coating composition that may contain a particular mobile compound means that the coating composition contains less than 100 parts per million (ppm) of the recited mobile compound. The term "essentially completely free" when used with respect to a coating composition that may contain a particular mobile compound means that the coating composition contains less than 5 parts per million (ppm) of the recited mobile compound. The term "completely free" when used with respect to a coating composition that may contain a particular mobile compound means that the coating composition contains less than 20 parts per billion (ppb) of the recited mobile compound. If the aforementioned phrases are used without the term "mobile" (e.g., "substantially free of BPA compound") then the disclosed compositions contain less than the aforementioned amount of the compound whether the compound is mobile in the coating or bound to a constituent of the coating.

Also herein, the recitations of numerical ranges by endpoints include all numbers subsumed within that range (e.g., 1 to 5 includes 1, 1.5, 2, 2.75, 3, 3.80, 4, 5, and the like).

A variety of compounds may be used to prepare the disclosed di(amido(alkyl)phenol) compounds, including, for example, compounds having both phenol and acid or phenol and ester functionalities. A preferred class of phenolic acids or esters has Formula IV shown below:

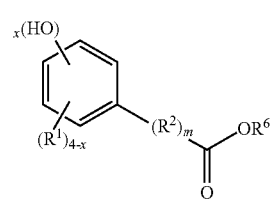

Formula IV wherein:

x, m, $R^1$ and $R^2$ are as defined above; and $R^6$ is hydrogen or a monovalent aliphatic group. $R^6$ may be linear or branched and may contain heteroatoms or aromatic rings. Preferably $R^6$ is hydrogen, methyl or ethyl.

Exemplary compounds with phenol and acid or ester functionalities include 2-hydroxybenzoic acid, 3-hydroxybenzoic acid, 4-hydroxybenzoic acid, hydroxyphenylacetate, hydroxyphenylpropionate, hydroxybenzoate, coumarin esters and the phenolic esters that may be obtained from coumarin itself. Preferred phenolic acids include 3-hydroxybenzoic acid, and preferred phenolic esters include hydroxyphenylacetate, hydroxybenzoate and coumarin.

A variety of diamines may be reacted with such phenolic acids or esters to prepare the disclosed di(amido(alkyl)phenol) compounds. A preferred class of diamines has Formula V shown below:

$H_2NR^3NH_2$      Formula V wherein $R^3$ is as defined above.

Exemplary diamines include branched or unbranched aliphatic diamines (for example, 1,2-diaminoethane, 1,3-diaminopropane, butane-1,4-diamine, pentane-1,5-diamine, 1,4-diamino-2-methylpentane, 1,5-diamino-2-methylpentane, hexane-1,6-diamine, 1,10-decanediamine and triethylenetetramine and its homologs); aliphatic diamines (for example, cyclohexyldiamine and tricyclodecane diamine); aromatic diamines (for example, xylylene diamine); amino-terminated polyamides (for example, adducts of a diamine and diacid such as the adduct of ethylene diamine and dimer fatty acids or their homologs); polyetherdiamines (for example, JEFFAMINE™ D, ED and EDR series polyetheramines from Huntsman Corporation) and dimer diamines (for example, PRIAMINE 1071, 1074 and 1075 dimer diamines from Croda International). Preferred diamines include branched aliphatic diamines such as 1,5-diamino-2-methylpentane, unbranched aliphatic diamines such as hexane-1,6-diamine, and amino-terminated polyamides.

The disclosed di(amido(alkyl)phenol) compounds may also be prepared using compounds having both phenol and amine functionalities. A preferred class of such compounds has Formula VI shown below:

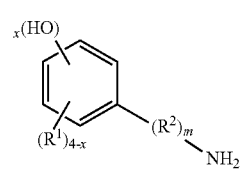

Formula VI wherein x, m, $R^1$ and $R^2$ are as defined above.

Exemplary phenolic amines include aminophenols, aminoethyl phenols, aminopropyl phenols, 4-(2-aminoethyl)

phenol) and 5-amino-2-methyl phenol. Preferred phenolic amines include aminoethyl phenols such as 3-(1-aminoethyl)phenol.

A variety of diacids or diesters may be reacted with such phenolic amines to prepare the disclosed di(amido(alkyl) phenol) compounds. A preferred class of diacids or diesters has Formula VII shown below:

  Formula VII wherein:

$R^3$ and $R^6$ are as defined above.

Exemplary diacids include aliphatic linear diacids such as ethanedioic acid, propanedioic acid, butanedioic acid, pentanedioic acid, hexanedioic acid, heptanedioic acid, octanedioic acid, nonanedioic acid, decanedioic acid, undecanedioic acid, dodecanedioic acid, mixtures of diacids, terephthalic acid, mixtures of acids, and isomers of the foregoing (for example maleic and fumaric acid). Preferred diacids include the various isomers of pentanedioic acid.

Exemplary diesters include aliphatic linear diesters such as ethanedioic acid dimethyl ester, propanedioic acid dimethyl ester, butanedioic acid dimethyl ester, pentanedioic acid dimethyl ester, hexanedioic acid dimethyl ester, heptanedioic acid dimethyl ester, octanedioic acid dimethyl ester, nonanedioic acid dimethyl ester, decanedioic acid dimethyl ester, undecanedioic acid dimethyl ester, dodecanedioic acid dimethyl ester, mixtures of diesters (for example, mixtures of succinates, and the glutarate:succinate: adipate mixture commercially available from Rhodia as RHODIASOLV™ RPDE), dimethyl terephthalate and its homologs; and dimer acid fatty diesters such as maleate and fumarate diesters.

Reactions to prepare the disclosed di(amido(alkyl)phenol) compounds may be performed using a variety of temperature and pressure conditions and a variety of types of equipment. The chosen conditions may be based on a variety of factors including the chosen, starting materials, the desired end use for the product and the available reaction vessel or vacuum stripping equipment. The reactions generally will be performed using appropriate stoichiometric amounts of each reactant, for example about a 2:1 ratio of phenolic acid or ester to diamine or phenolic amine to diacid or diester, with wider ranges (for example, about 2.3:1 to 2.7:1) being useful in some circumstances. The resulting di(amido(alkyl)phenol) product compounds may for example have a number average molecular weight (Mn) of about 300 up to about 1500, or up to about 1000 or up to about 500 Daltons (Da) as evaluated using gel permeation chromatography and a polystyrene standard.

When the starting materials used to prepare the disclosed di(amido(alkyl)phenol) compounds are each in liquid form at the desired reaction temperature, or can be combined with one another to form a liquid mixture at such reaction temperature, then the reaction may if desired be performed neat, without added solvent(s). If employed, solvent(s) may be added to the reaction vessel before beginning the starting material feed(s), may be added together with the starting material feed(s) or may be added to the reaction vessel as a separate feed. The selection of a particular solvent and its level of addition may be based on a variety of factors including the chosen starting materials, the desired end use for the product and the available reaction vessel or vacuum stripping equipment. In general, it is preferred to use as little solvent as possible to reduce separation and recovery requirements and minimize the formation of contaminants or, in some instances, undesired oligomers (e.g., dimers or trimers). Solvents may however permit a lower reaction temperature to be employed (e.g., by acting as a heat sink to prevent run-away reactions and reduce cooling requirements), may reduce stirrer torque, may provide a less viscous or more plasticized final product, may reduce the molecular weight and may help remove alcohol by forming an azeotrope. Solvents in which the reactants or the reaction product are insoluble may be employed to facilitate separation or purification of the reaction produce. Desirably, the chosen solvent(s) are not unduly reactive with the starting materials or product di(amido(alkyl)phenol) compounds and do not unduly decompose under the chosen reaction conditions. Alcohols are desirably avoided, as they may react with the starting materials and the reaction normally will be accelerated by removal of alcohols. Higher boiling solvents are preferred due to their low, vapor pressure at high temperatures, e.g., solvents with a boiling point above 100° C. or above 150° C. Exemplary solvents that may be used include aromatic hydrocarbons including toluene (B.P. 110° C.), xylene (B.P. 140° C.), commercially-available materials such as the "AROMATIC" series fluids (e.g., AROMATIC 150 and AROMATIC 200) from ExxonMobil Corp., the SHELLSOL™ series fluids (e.g., SHELLSOL A100 and SHELLSOL A150) from Shell Chemical Co, HYDROSOL A170 (B.P. 140-200° C.) from DHC SolventChemie GmbH, and mixtures thereof; petroleum solvents including petroleum naphtha, VM&P naphtha, Stoddard solvent, kerosene (B.P. 150° C.) and mixtures thereof, ketones including methyl isobutyl ketone (B.P. 117° C.), methyl isoamyl ketone (B.P. 144° C.), methyl amyl ketone (B.P. 150° C.), cyclohexanone (B.P. 156° C.), isobutyl ketone (B.P. 168° C.), methyl hexyl ketone (B.P. 173° C.), methyl heptyl ketone (B.P. 192° C.) and mixtures thereof, and the series of glyme and diglyme solvents available from Clariant Corporation. When used, the solvent amount may vary over a wide range, and may for example represent about 5 to about 98 wt. %, about 10 to 80 wt. %, or about 30 to about 50 wt. % of the reaction mixture.

One or more catalysts preferably are employed to assist in converting the starting materials to the disclosed di(amido (alkyl)phenol) compounds. Exemplary catalysts include transesterification and amination catalysts that will be familiar to persons skilled in the art. The catalyst may be heterogeneous (viz., a solid that contacts a reaction mixture which may be in liquid, gas or other fluid form), homogeneous (viz., a catalyst that dissolves in the reaction mixture), or a combination thereof. The catalyst may be unsupported or may be supported on a variety of substrates that will be familiar to persons having ordinary skill in the art. Recovery or regeneration procedures that will likewise be familiar to persons having ordinary skill in the art may be employed to enable catalyst reuse. Exemplary catalysts and catalytic supports include those described in International Application Nos. WO 2012/064483 A1 and WO 2012/064484 A1 and in the patents and patent applications cited therein. Preferred catalysts include soluble-catalysts based on organic titanates or zirconates (for example, tetrabutyl zirconate, titanium isopropoxide, TYZOR™ AC422 and TYZOR PC-64 catalysts available from Dorf Ketal, and 2-hydroxypyridine). The catalyst type and amount may vary based on a variety of factors including the chosen starting materials, the desired end use for the product and the chosen reaction vessel. Under batch conditions, the catalyst amount may for example be about 0.1 to about 20 wt. % or about 1 to about 15 wt. % catalyst per 100 parts by weight of reactive starting materials. Under continuous conditions, the starting material space velocities typically will be adjusted to provide the desired degree of catalyst exposure, product yield and selectivity.

The reaction temperature may for example be maintained below about 200° C., and preferably below about 180° C. and more preferably at about 130° C. to about 180° C. Below these preferred temperatures the reaction may be too slow to be practical for commercial scale production. Above these preferred temperatures, selectivity may be reduced and undesired byproducts may be obtained or obtained in undesired amounts. In a preferred method the reaction is performed at ambient pressure using reflux to remove alcohols and other byproducts.

The resulting di(amido(alkyl)phenol) compounds may be used as is or purified prior to use. In general the use of a purification method may depend on factors including the chosen reaction scheme, yield, byproducts and the form (e.g., solid or liquid) in which the product is obtained. Exemplary purification methods will be familiar to persons having ordinary skill in the art and include washing with solvent, solvent extraction, flotation, filtration, centrifugation, evaporation, crystallization, recrystallization, fractionation, electrolysis, sublimation, adsorption, distillation and biological methods including fermentation, microbes and enzymes. Preferably the product is a solid and may be purified by washing with a solvent for one or more of the starting materials.

The disclosed di(amido(alkyl)phenol) compounds provide useful raw or starting materials for the preparation of a variety of homopolymers and copolymers. For example, compounds of Formulas I, II or III may be reacted with an epoxide (for example, epichlorohydrin) to form a diepoxide analog of compounds of Formulas I, II or III (viz., a diglycidyl ether or "DGE") with oxirane terminal groups. The resulting compounds may then be reacted with any suitable extender bearing two identical or different oxirane-reactive groups (for example hydroxyl groups, hydroxyphenyl groups, acid groups or amine groups) or with combinations of extenders to build molecular weight. Compounds containing hydroxyphenyl groups (for example, dihydric phenols) are preferred extenders which can be reacted with the diepoxide analogs of the compounds of Formulas I, II or III to provide polymers that include —$CH_2$—CH(OH)—$CH_2$— or —$CH_2$—$CH_2$—CH(OH)— segments and which have upgraded molecular weights compared to the Formula I, II or III starting compound. In some embodiments, the extender is a compound of Formula I, II or III. Other suitable extenders include hindered diphenols (for example, 4,4'-methylenebis(2,6-dimethylphenol) as described in U.S. application Ser. No. 13/570,743 (Niederst et al. '743); nonsubstituted diphenols having low estrogenicity (for example, 4,4'-(1,4-phenylenebis(propane-2,2-diyl))diphenol and 2,2'methylenebis(phenol)) as also described in Niederst et al. '743; diphenols such as those described (for example, the bis-4-hydroxybenzoate of cyclohexanedimethanol) in U.S. Pat. No. 8,129,495 B2 (Evans et al. '495); and the dihydric compounds of Formula E shown below:

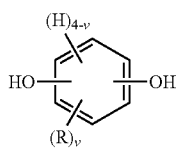

Formula E wherein:
each R, if present, is preferably independently an atom or group preferably having atomic weight of at least 15 Daltons that is preferably substantially nonreactive with an epoxy group;
v is 0 to 4; and
two or more R groups can optionally join to form one or more cyclic groups.

Exemplary dihydric compounds of Formula E include catechol and substituted catechols (e.g., 3-methylcatechol, 4-methylcatechol, 4-tert-butyl catechol, and the like); hydroquinone and substituted hydroquinones (e.g., methylhydroquinone, 2,5-dimethylhydroquinone, trimethylhydroquinone, tetramethylhydroquinone, ethylhydroquinone, 2,5-diethylhydroquinone, triethylhydroquinone, tetraethylhydroquinone, tert-butylhydroquinone, 2,5-di-tert-butylhydroquinone, and the like); resorcinol and substituted resorcinols (e.g., 2-methylresorcinol, 4-methyl resorcinol, 2,5-dimethylresorcinol, 4-ethylresorcinol, 4-butylresorcinol, 4,6-di-tert-butylresorcinol, 2,4,6-tri-tert-butylresorcinol, and the like); and variants and mixtures thereof. Additional suitable dihydric compounds are disclosed in U.S. Patent Application Publication No. US 2013/0206756 A1 (Niederst et al. '756) and International Application No. WO 2013/119686 A1 (Niederst et al. '686).

Compounds of Formulas I, II or III may also be reacted with diepoxides to provide polymers that include —$CH_2$—CH(OH)—$CH_2$— or —$CH_2$—$CH_2$—CH(OH)— segments and which have upgraded molecular weights compared to the Formula I, II or III starting compound. Exemplary such diepoxides include those based on bisphenol A, bisphenol F, and preferably those based on any of a variety of non-Bisphenol A ("non-BPA") and non-bisphenol F ("non-BPF") compounds including those described in the above-mentioned Evans et al. '495 patent and in the Niederst et al. '743, Niederst et al. '756 and Niederst et al. '686 applications. By way of example, exemplary non-BPA and non-BPF epoxides include the diepoxide analogs of compounds of Formula I and Formula II; diglycidyl ethers of hindered diphenols (for example, 4,4'-methylenebis(2,6-dimethylphenol diglycidyl ether) as described in Niederst et al. '743; diglycidyl ethers of nonsubstituted diphenols having low estrogenicity (for example, 4,4'-(1,4-phenylenebis(propane-2,2-diyl))diphenol diglycidyl ether and 2,2'methylenebis(phenol) diglycidyl ether) as also described in Niederst et al. '743; diglycidyl ethers of diphenols such as those described (for example, bis-4-hydroxybenzoate of cyclohexanedimethanol diglycidyl ether) in Evans et al. '495; diglycidyl ethers of compounds of Formula E shown above (preferably substituted such compounds); 1,4-cyclohexanedimethanol diglycidyl ether (CHDMDGE); resorcinol diglycidyl ether; neopentyl glycol diglycidyl ether; 2-methyl-1,3-propandiol diglycidyl ether, and diepoxides of cyclic diols such as cyclobutanediol (e.g., the diglycidyl ether of 2,2,4,4-tetramethyl-1,3-cyclobutanediol) and tricyclodecane dimethanol (e.g., the diglycidyl ether of tricyclodecane dimethanol). The resulting polymers may be formulated with various additional ingredients to provide coatings for rigid or flexible packaging, as well as a variety of other uses. Conditions for the epoxy reactions are generally carried out using standard techniques that will be known to persons having ordinary skill in the art. For example, a di(amido(alkyl)phenol) of Formula I may be reacted with a suitable halogenated epoxy such as epichlorohydrin to provide the diglycidylether-terminated diamide shown below in Formula VIII:

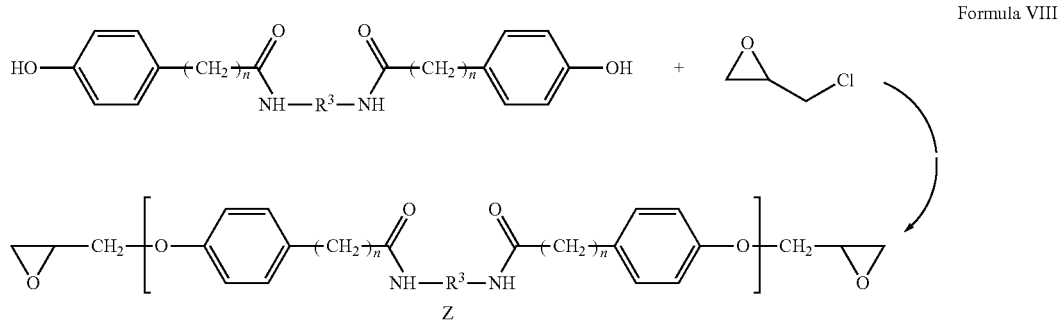

Formula VIII wherein n and $R^3$ are as defined above. The reaction preferably is performed in an alkaline medium. The desired alkalinity is obtained by adding basic substances, such as sodium or potassium hydroxide, preferably in stoichiometric excess to the epichlorohydrin. The reaction is preferably carried out at temperatures of 50° C. to 150° C. Heating is preferably continued for several hours to effect the reaction and the product is then washed free of salt and base. Procedures for similar reactions are disclosed, for example, in U.S. Pat. No. 2,633,458.

In Formula VIII, the identifier Z denotes a segment of the polymer chain enclosed in brackets. Segment Z may in general be a compound derived by removal of the terminal phenol hydrogen atoms from any of the compounds of Formulas I, II or III, and is shown below as segment Z':

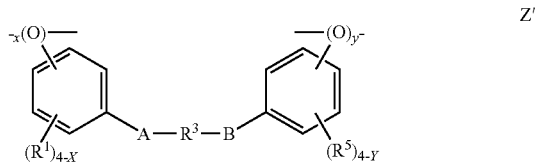

Z' wherein A, B, x, y, $R^1$, $R^3$ and $R^5$ are as defined above. In embodiments for which x or y is greater than 1, the resulting Segments Z' will be part of a branched structure. In an embodiment, A and B are the same. In another embodiment, A and B are the same and are arranged in mirror image fashion with respect to $R^3$. In another embodiment, A is $-R^2_m CONH-$ and B is $-NHCOR^2_m-$ or A is $-R^2_m NHCO-$ and B is $-CONHR^2_m-$ wherein m and $R^2$ are as defined above.

Segment Z' may for example have a molecular weight of about 300 to about 1500 and may be present more than once in an upgraded molecular weight polymer made using the disclosed di(amido(alkyl)phenol) compounds. For example, the Formula VIII diglycidylether-terminated diamide may be reacted with a diphenol such as a compound of Formula I or II or diphenols such as those described in the above-mentioned Evans et al. '495 patent and in the Niederst et al. '743, Niederst et al. '756 and Niederst et al. '686 applications to provide a polyether having upgraded molecular weight. Depending on stoichiometry, the resultant polyether may be epoxy-terminated or phenoxy-terminated, and may have a variety of molecular weights, such as the molecular weights of commercially available BPA-based epoxy materials (e.g., those available under trade designations such as EPON 828, 1001, 1007 and 1009 from Resolution Performance Products, Houston, Tex.). Preferred upgraded molecular weight polymers (for example, upgraded molecular weight polyethers) have a number average molecular weight (Mn) of at least 2,000, more preferably at least 3,000, and even more preferably at least 4,000. The molecular weight of the upgraded molecular weight polymer may be as high as is needed for the desired application.

If desired, one or more comonomers or co-oligomers may also be included with the reactants used to generate the disclosed polymers. Non-limiting examples of such comonomers or co-oligomers include adipic acid, azelaic acid, terephthalic acid, isophthalic acid, and combinations thereof. The comonomers or co-oligomers may for example be included in an initial reaction mixture of polyepoxide and extender (e.g., polyhydric phenol) or may be post-reacted with the resulting polyether oligomer or polymer. In presently preferred embodiments, a comonomer or co-oligomer are not utilized to produce the disclosed polymers.

Molecular weight advancement may be enhanced by the use of a suitable catalyst in an amount sufficient to facilitate the desired reaction. For example, in the condensation reaction of a diepoxide (whether it be a diepoxide analog of Formulas I, II or III or another diepoxide) with a compound of Formulas I, II or III, exemplary catalysts include amines, hydroxides (e.g., potassium hydroxide), phosphonium salts, and the like. A presently preferred catalyst is a phosphonium catalyst.

The disclosed epoxy-terminated polymers may be reacted with a variety of other reactive materials to form desirable products. For example, the epoxy-terminated polymers may be reacted with fatty acids to form polymers having unsaturated (e.g., air oxidizable) reactive groups, or with acrylic acid or methacrylic acid to form free radically curable polymers. The epoxy-terminated polymers may also be reacted with a suitable diacid (such as adipic acid) to further advance the polymer molecular weight.

The disclosed di(amido(alkyl)phenol) compounds, and the disclosed upgraded molecular weight phenoxy-terminated compounds, may also be reacted with a variety of other reactive materials to form desirable products. For example, they may be reacted with cyclic carbonates such as ethylene carbonate or propylene carbonate to produce polyols. The polyols may if desired be further reacted with a suitable polyacid (for example isophthalic acid) and if need be additional polyol (for example, ethylene glycol) to make polyesters. Exemplary polyacid and polyol reactants and reaction conditions will be familiar to persons having ordinary skill in the art, and include materials and conditions such as those described in U.S. Pat. No. 6,974,631 B2 (Hayes et al.) and U.S. Pat. No. 7,381,472 B2 (Brandenburger et al.) and in published International Application No. WO 2010/075395 A2 (Martinoni et al.). The polyols may also be reacted with isocyanates to produce polyurethanes. Exemplary isocyanates and reaction conditions will also be familiar to persons having ordinary skill in the art.

The disclosed di(amido(alkyl)phenol) compounds, and the disclosed upgraded molecular weight phenoxy-terminated compounds, may also be reacted with phosgene to provide polycarbonates. Exemplary reaction conditions will for making such polycarbonates are described in International Application No. PCT/US2013/032262 (Niederst et al.), and will also be familiar to persons having ordinary skill in the art.

The disclosed di(amido(alkyl)phenol) compounds, and the disclosed upgraded molecular weight phenoxy-terminated compounds, may also be reacted with a variety of aldehydes (for example, formaldehyde) in a condensation reaction to provide phenolic resins. Exemplary aldehydes and reaction conditions will be familiar to persons having ordinary skill in the art, and include materials and conditions such as those described in U.S. Patent Application Publication number US 2011/0315591 A1 (Lespinasse et al.).

The disclosed upgraded molecular weight polymers may be applied to a variety of substrates as liquid or powder-based coating compositions. Liquid coating compositions (typically including the polymer and a liquid carrier) may be preferred for many and uses, especially for use on heat-sensitive substrates or for substrates where an especially thin coating is desired. Exemplary liquid carriers include water, organic solvents, and mixtures of liquid carriers. Exemplary organic solvents include glycol ethers, alcohols, aromatic or aliphatic hydrocarbons, dibasic esters, ketones, esters, and the like. Preferably, such carriers are selected to provide a dispersion or solution of the polymer with which additional additives may be combined to provide a final coating formulation. In one embodiment, the disclosed liquid coating compositions are solvent-based systems that include no more than a de minimus amount of water (e.g., less than 2 wt. % of water). The disclosed solvent-based liquid coating compositions may for example contain at least 20 wt. % non-volatile components (viz., "solids"), and more preferably at least 25 wt. % non-volatile components. The disclosed solvent-based liquid coating compositions may also for example contain no greater than 50 wt. % non-volatile components, and more preferably no greater than 40 wt. % non-volatile components. For such an organic solvent-based composition, the non-volatile film-forming components preferably include at least 50 wt. % of the disclosed upgraded molecular weight polymer, more preferably at least 55 wt. % of the polymer, and even more preferably at least 60 wt. % of the polymer. For such an organic solvent-based composition, the non-volatile film-forming components preferably include no greater than 95 wt. % of the disclosed upgraded molecular weight polymer, and more preferably no greater than 85 wt. % of the polymer.

Water-based systems may be made for example as described in U.S. Pat. Nos. 3,943,187, 4,076,676, 4,212,781, 4,247,439, 4,285,847, 4,413,015, 4,446,258, 4,517,322, 4,963,602, 5,296,525, 5,527,840, 5,830,952, 5,922,817, 7,189,787 and 8,092,876 and in U.S. Patent Application Publication No. US 2005/0196629 A1. Water-based coating systems may optionally include one or more organic solvents, which will typically be selected to be miscible in water. The liquid carrier system of a water-based coating composition will typically include at least 50 wt. % water, more typically at least 75 wt. % water, and in some embodiments more than 90 wt. % or more than 95 wt. % water. Any suitable technique may be used to render the disclosed polymers miscible in water. For example, the polymer may include a suitable amount of salt groups such as ionic or cationic salt groups (or groups capable of forming such salt groups) to render the polymer miscible in water. Neutralized acid or base groups are preferred salt groups. For example, a water-dispersible polymer may be formed by combining an epoxy-terminated polymer and an acid-functional polymer in the presence of an amine or other suitable base (more preferably a tertiary amine). If desired, the acid-functional polymer may be combined with an amine (for example a tertiary amine) to at least partially neutralize the polymer prior to reaction with the epoxy-terminated polymer. In another embodiment, a water-dispersible free radically-polymerizable polymer may be formed by reacting an epoxy-terminated polymer with an ethylenically-unsaturated acidic monomer to form an acid-functional polymer, which may then be neutralized, for example, with an amine or other suitable base (more preferably a tertiary amine). If desired, an anhydride may be used in place of the acidic monomer. This will also provide acid functionality which, when combined with an amine to at least partially neutralize the acid functionality, will make the product water-dispersible. In some embodiments, the disclosed coating compositions are substantially free of acrylic materials, for example they may contain less than about 1 wt. % polymerized acrylic monomers. The disclosed water-based compositions may for example contain at least 15 wt. % non-volatile components. The disclosed water-based compositions may also for example contain no greater than 50 wt. % non-volatile components, and more preferably no greater than 40 wt. % non-volatile components. For such a water-based composition, the non-volatile film-forming components preferably include at least 5 wt. % of the disclosed upgraded molecular weight polymer, more preferably at least 25 wt. % of the polymer, even more preferably at least 30 wt. % of the polymer, and optimally at least 40 wt. % of the polymer. For such a water-based composition, the non-volatile film forming components preferably include no greater than 70 wt. % of the disclosed upgraded molecular weight polymer, and more preferably no greater than 60 wt. % of the polymer.

The disclosed polymers may serve as a binder polymer in the disclosed coating compositions. The binder polymer amount may vary widely depending on a variety of considerations including the method of application, the presence of other film-forming materials, whether the coating composition is a water-based or solvent-based system, and so on. For liquid-based coating compositions, the binder polymer will typically constitute at least 10 wt. %, more typically at least 30 wt. %, and even more typically at least 50 wt. % of the coating composition, based on the total weight of resin solids in the coating composition. For such liquid-based coating compositions, the binder polymer will typically constitute less than about 90 wt. %, more typically less than about 80 wt. %, and even more typically less than about 70 wt. % of the coating composition, based on the total weight of resin solids in the coating composition.

Preferred coating compositions are substantially free of mobile BPA and mobile bisphenol A diglycidyl ether (BADGE), and more preferably are essentially free of these compounds, and most preferably are completely free of these compounds. The disclosed coating composition is also preferably substantially free of bound BPA and bound BADGE, more preferably essentially free of these compounds, and most preferably completely free of these compounds.

When the disclosed coating compositions include polymers having suitable reactive groups (for example, epoxy groups, phenoxy groups or ethylenically unsaturated groups), the coating composition preferably also is formulated using one or more optional curing agents (for example, crosslinking resins, sometimes referred to as "crosslinkers"). The choice of a particular crosslinker typically depends on the particular product being formulated. For example, some coating compositions are highly colored (e.g., gold-colored coatings). These coatings may typically be formulated using crosslinkers that themselves tend to have a yellowish color. In contrast, white coatings are generally formulated using non-yellow or non-yellowing crosslinkers, or only a small amount of a yellow or yellowing crosslinker.

Preferred curing agents are substantially free of mobile BPA and mobile BADGE and more preferably completely free of bound BPA and bound BADGE. Suitable examples of such curing agents for use with phenoxy group-containing polymers include hydroxyl-reactive curing resins such as phenoplasts, aminoplast, blocked or unblocked isocyanates, or mixtures thereof.

Exemplary phenoplast resins include the condensation products of aldehydes with phenols. Formaldehyde and acetaldehyde are preferred aldehydes. Various phenols can be employed including phenol, cresol, p-phenylphenol, p-tert-butylphenol, p-tert-amylphenol and cyclopentylphenol.

Exemplary aminoplast resins are the condensation products of aldehydes such as formaldehyde, acetaldehyde, crotonaldehyde, and benzaldehyde with amino- or amido-group-containing substances such as urea, melamine, and benzoguanamine. Examples of suitable aminoplast cross-linking resins include, without limitation, benzoguanamine-formaldehyde resins, melamine-formaldehyde resins, etherified melamine-formaldehyde, and urea-formaldehyde resins.

Exemplary other generally suitable curing agents include blocked or non-blocked aliphatic, cycloaliphatic or aromatic di-, tri-, or polyvalent isocyanates, such as hexamethylene diisocyanate, cyclohexyl-1,4-diisocyanate, and the like. Further non-limiting examples of generally suitable blocked isocyanates include isomers of isophorone diisocyanate, dicyclohexylmethane diisocyanate, toluene diisocyanate, diphenylmethane diisocyanate, phenylene diisocyanate, tetramethyl xylene diisocyanate, xylylene diisocyanate, and mixtures thereof. In some embodiments, blocked isocyanates having an Mn of at least about 300, more preferably at least about 650, and even more preferably at least about 1,000 may be used. Polymeric blocked isocyanates are useful in certain embodiments. Exemplary polymeric blocked isocyanates include a biuret or isocyanurate of a diisocyanate, a trifuncrional "trimer", or a mixture thereof. Commercially available blocked polymeric isocyanates include TRIXENE™ BI 7951, TRIXENE BI 7984, TRIXENE BI 7963, TRIXENE BI 7981 (available from Baxenden Chemicals, Ltd., Accrington, Lancashire, England); DESMODUR™ BL 3175A, DESMODUR BL3272, DESMODUR BL3370, DESMODUR BL 3475, DESMODUR BL 4265, DESMODUR PL 340, DESMODUR VP LS 2078, DESMODUR VP LS 2117, and DESMODUR VP LS 2352 (available from Bayer Corp., Pittsburgh, Pa., USA); and combinations thereof. Exemplary trimers include a trimerization product prepared from on average three diisocyanate molecules or a trimer prepared from on average three moles of diisocyanate (e.g., HMDI) reacted with one mole of another compound such as, for example, a triol (e.g., trimethylolpropane).

The level of curing agent (viz., crosslinker) used will typically depend on the type of curing agent, the time and temperature of the bake, and the molecular weight of the binder polymer. If used, the crosslinker is typically present in an amount of up to 50 wt. %, preferably up to 30 wt. %, and more preferably up to 15 wt. % based on the total weight of the resin solids in the coating composition. If used, a crosslinker is preferably present in an amount of at least 0.1 wt. %, more preferably at least 1 wt. %, and even more preferably at least 1.5 wt. % based upon the total resin solids weight.

The disclosed coating compositions may also include other optional polymers that do not adversely affect the coating composition or a cured coating thereof. Such optional polymers are typically included as a nonreactive filler material, although they may be included as a reactive crosslinker, or to provide other desired properties. Such optional nonreactive filler polymers include, for example, polyesters, acrylics, polyamides, polyethers, and novalacs. Alternatively, such additional polymeric materials or monomers may be reactive with other components of the composition (e.g., an acid-functional or unsaturated polymer). If desired, reactive polymers may be incorporated into the disclosed compositions, for example to provide additional functionality for various purposes, including crosslinking or to assist in dispersing the disclosed upgraded molecular weight polymers into water. Examples of such reactive polymers include, for example, functionalized polyesters, acrylics, polyamides, and polyethers. Preferred optional polymers are substantially free of mobile BPA and mobile BADGE, and more preferably completely free of such compounds.

Another preferred optional ingredient is a catalyst to increase the rate of cure. Examples of catalysts, include, but are not limited to, strong acids including phosphoric acid, dodecylbenzene sulfonic acid (DDBSA, available as CYCAT 600 from Cytec), methane sulfonic acid (MSA), p-toluene sulfonic acid (pTSA), dinonylnaphthalene disulfonic acid (DNNDSA), and triflic acid; quaternary ammonium compounds; phosphorous compounds; and tin, titanium, and zinc compounds. Specific examples include, but are not limited to, a tetraalkyl ammonium halide, a tetraalkyl or tetraaryl phosphonium iodide or acetate, tin octoate, zinc octoate, triphenylphosphine, and similar catalysts known to persons having ordinary skill in the art. If used, a catalyst is preferably present in an amount of at least 0.01 wt. %, and more preferably at least 0.1 wt. %, based on the weight of nonvolatile material in the coating composition. If used, a catalyst is preferably present in an amount of no greater than 3 wt. %, and more preferably no greater than 1 wt. %, based on the weight of nonvolatile material in the coating composition.

Another useful optional ingredient is a lubricant (e.g., a wax), which facilitates manufacture of fabricated metal articles (e.g., container closures and food or beverage can ends) by imparting lubricity to sheets of coated metal substrate. Non-limiting examples of suitable lubricants include, for example, natural waxes such as Carnauba wax or lanolin wax, polytetrafluoroethane (PTFE) and polyethylene-type lubricants. If used, a lubricant is preferably present in the coating composition in an amount of at least 0.1 wt. %, and preferably no greater than 2 wt. %, and more preferably no greater than 1 wt. %, based on the total weight of nonvolatile material in the coating composition.

Another useful optional ingredient is a pigment, such as titanium dioxide. If used, a pigment is present in the disclosed coating composition in an amount of no greater than 70 wt. %, more preferably no greater than 50 wt. %, and even more preferably no greater than 40 wt. %, based on the total weight of solids in the coating composition.

Surfactants may optionally be added to the disclosed coating composition to aid in flow and wetting of a substrate. Examples of surfactants include, but are not limited to, nonylphenol polyethers and salts and similar surfactants known to persons having ordinary skill in the art. If used, a surfactant is preferably present in an amount of at least 0.01 wt. %, and more preferably at least 0.1 wt. %, based on the weight of resin solids. If used, a surfactant is preferably present in an amount no greater than 10 wt. %, and more preferably no greater than 5 wt. %, based on the weight of resin solids.

The disclosed coating compositions may also include other optional ingredients that do not adversely affect the coating composition or cured coating thereof. Such optional ingredients are typically included in a coating composition to enhance composition esthetics; to facilitate manufacturing, processing, handling, or application of the composition; or to further improve a particular functional property of a coating composition or a cured coating thereof. For example, the disclosed coating compositions may optionally include fillers other than those already mentioned, dyes, colorants, toners, coalescents, extenders, anticorrosion agents, flow control agents, thixotropic agents, dispersing agents, antioxidants, oxygen-scavenging materials, adhesion promoters, light stabilizers, and mixtures thereof, as required to provide desired film properties. Each optional ingredient is preferably included in a sufficient amount to serve its intended purpose, but not in such an amount to adversely affect a coating composition or a cured coating thereof.

The disclosed coating compositions may be present as a layer of a mono-layer coating system or as one or more layers of a multi-layer coating system. The coating composition can be used as a primer coat, an intermediate coat, a top coat, or a combination thereof. The coating thickness of a particular layer and of the overall coating system will vary depending upon the coating material used, the substrate, the coating application method, and the end use for the coated article. Mono-layer or multi-layer coil coating systems including one or more layers formed from the disclosed coating composition may have any suitable overall coating thickness, but will typically have an overall average dry coating thickness of from about 2 to about 60 micrometers and more typically from about 3 to about 12 micrometers.

The disclosed coating compositions may be applied to a substrate either prior to, or after, the substrate is formed into an article such as, for example, a food or beverage container or a portion thereof. In one embodiment, a method of forming food or beverage cans is provided that includes: applying a coating composition described herein to a metal substrate (e.g., applying the composition to the metal substrate in the form of a planar coil or sheet), hardening the composition, and forming (e.g., via stamping) the substrate into a packaging container or a portion thereof (e.g., a food or beverage can or a portion thereof). For example, two-piece or three-piece cans or portions thereof such as riveted beverage can ends with a cured coating of the disclosed coating composition on a surface thereof can be formed in such a method. In another embodiment, a method of forming food or beverage cans is provided that includes: forming (e.g., via stamping) a metal substrate into a packaging container or a portion thereof (e.g., a food or beverage can or a portion thereof), applying a coating composition described herein to the inside, outside or both inside and outside portions of such packaging container or a portion thereof, and hardening the composition. The disclosed upgraded molecular weight polymers are especially desirable for use on the inside or interior portion of such food or beverage containers, and for other applications involving a food or beverage contact surface or involving a metal substrate. Exemplary such applications include two-piece drawn food cans, three-piece food cans, food can ends, drawn and ironed food or beverage cans, beverage can ends, easy open can ends, twist-off closure lids, and the like.

After applying the coating composition onto a substrate, the composition can be cured using a variety of processes, including, for example, oven baking by either conventional or convectional methods, or any other method that provides an elevated temperature suitable for curing the coating. The curing process may be performed in either discrete or combined steps. For example, substrates can be dried at ambient temperature to leave the coating compositions in a largely uncrosslinked state. The coated substrates can then be heated to fully cure the compositions. In certain instances, the disclosed coating compositions may be dried and cured in one step.

The cure conditions will vary depending upon the method of application and the intended end use. The curing process may be performed at any suitable temperature, including, for example, oven temperatures in the range of from about 100° C. to about 300° C., and more typically from about 177° C. to about 250° C. If a metal coil is the substrate to be coated, curing of the applied coating composition may be conducted, for example, by heating the coated metal substrate over a suitable time period to a peak metal temperature ("PMT") of preferably greater than about 177° C. More preferably, the coated metal coil is heated for a suitable time period (e.g., about 5 to 900 seconds) to a PMT of at least about 218° C.

The following examples are offered to aid in understanding the disclosed compounds, compositions and methods and are not to be construed as limiting the scope thereof. Unless otherwise indicated, all parts and percentages are by weight. Polymers such as those described in the Examples may be evaluated using a variety of tests including:

Solvent Resistance

The extent of "cure" or crosslinking of a coating may be measured as a resistance to solvents, such as methyl ethyl ketone (MEK) or isopropyl alcohol (IPA). This test is performed as described in ASTM D5402-93. The number of double-rubs (i.e., one back-and forth motion) is reported.

Global Extractions

The global extraction test is designed to estimate the total amount of mobile material that can potentially migrate out of a coating and into food packed in a coated can. Typically a coated substrate is subjected to water or solvent blends under a variety of conditions to simulate a given end use. Acceptable extraction conditions and media can be found in 21 CFR section 175.300, paragraphs (d) and (e). The current allowable global extraction limit as defined by this FDA regulation is 50 parts per million (ppm). Extraction may be evaluated using the procedure described in 21 CFR section 175.300, paragraph (e) (4) (xv) but with the following modifications to ensure worst-case scenario performance: 1) the alcohol content is increased to 10% by weight and 2) the filled containers are held for a 10-day equilibrium period at 37.8° C. These modifications are per the FDA publication "Guidelines for Industry" for preparation of Food Contact Notifications. The coated beverage can is filled with 10 wt. % aqueous ethanol and subjected to pasteurization conditions (65.6° C.) for 2 hours, followed by a 10-day equilibrium period at 37.8° C. Determination of the amount of extractives is determined as described in 21 CFR section 175.300, paragraph (e) (5), and ppm values are calculated based on surface area of the can (no end) of 283.9 cm² with a volume of 355 milliliters (ml). Preferred coatings give global extraction results of less than 50 ppm, more preferred results of less than 10 ppm, and even more preferred results of less than 1 ppm. Most preferably, the global extraction results are optimally non-detectable.

Adhesion

Adhesion testing may be performed to assess whether the coating adheres to the coated substrate. The adhesion test is performed according to ASTM D3359, Test Method B, using SCOTCH™ 610 tape (available from 3M Company of Saint Paul, Minn.). Adhesion is generally rated on a scale of 0-10 where a rating of "10" indicates no adhesion failure, a rating of "9" indicates 90% of the coating remains adhered, a rating of "8" indicates 80% of the coating remains adhered, and so on. Adhesion ratings of 10 are typically desired for commercially viable coatings.

Blush Resistance

Blush resistance measures the ability of a coating to resist attack by various solutions. Typically, blush is measured by the amount of water absorbed into a coated film. When the film absorbs water, it generally becomes cloudy or looks white. Blush is generally measured visually using a scale of 0-10 where a rating of "10" indicates no blush and a rating of "0" indicates complete whitening of the film. Blush ratings of at least 7 are typically desired for commercially viable coatings and optimally 9 or above.

Process or Retort Resistance

This is a measure of the coating integrity of the coated substrate after exposure to heat and pressure with a liquid such as water. Retort performance is not necessarily required for all food and beverage coatings, but is desirable for some product types that are packed under retort conditions. Testing is accomplished by subjecting the coated substrate to heat ranging from 105° C. to 130° C. and pressure ranging from 0.7 kg/cm² to 1.05 kg/cm² for a period of 15 minutes to 90 minutes. For the present evaluation, the coated substrate may be immersed in deionized water and subjected to heat of 121° C. and pressure of 1.05 kg/cm² for a period of 90 minutes. The coated substrate may then be tested for adhesion and blush as described above. In food or beverage applications requiring retort performance, adhesion ratings of 10 and blush ratings of at least 7 are typically desired for commercially viable coatings.

Crazing—Reverse Impact Resistance

Reverse impact resistance measures the ability of a coated substrate to withstand the deformation encountered when impacted by a steel punch with a hemispherical head. For the present evaluation, a coated substrate may be subjected to 6.35 N-m of force using a BYK-GARDNER™ "Coverall" Bend and Impact Tester (available from Byk-Gardner, Inc.) and rated visually for micro-cracking or micro-fracturing—commonly referred to as crazing. Test pieces are impacted on the uncoated or reverse side. A rating of 10 indicates no craze and suggests sufficient flexibility and cure. A rating of 0 indicates complete failure. Commercially viable coatings preferably show slight or no crazing on a reverse impact test.

Wedge Bend Test

Coating flexibility was evaluated using an ERICHSEN™ Model 471 Bend and Impact Tester (available from Erichsen GmbH & Co. KG) and the manufacturer's recommended test procedure, except that the coated panels were 8×12 cm rather than 5×14 cm. The results were reported as the unruptured coating length as a percent of the overall coating fold line. In general, a value of at least 75% represents good performance and a value of 90% or more represents excellent performance.

206 End Fabrication

This test is a measure of fabrication ability of a coating. Standard size 206 can ends are formed in a press from coated steel plate. The ends are evaluated for initial failure. The ends are then soaked for 10 minutes in a copper sulfate solution containing 69 parts deionized water, 20 parts anhydrous copper sulfate, 10 parts concentrated hydrochloric acid and 1 part DOWFAX™ 2A1 surfactant (available from Dow Chemical Company). The percentage of the end circumference that is uncorroded is recorded.

206 End Coating Porosity

This test is a measure of coating porosity after forming. Coated size 206 can ends are prepared as described above. The ends are immersed in various solutions and subjected to retort conditions as described above. An electrode is placed atop the coating and a milliamp meter is used to measure current flow from the substrate to the electrode. The results are reported in milliamps of current flow.

Food Simulant Tests

The resistance properties of stamped standard size 202 ends formed from coated plate were evaluated by processing (retorting) them in three food simulants for 60 minutes at 121° C. and 1.05 kg/cm². The three food simulants were deionized water, a 1% by weight solution of lactic acid in deionized water and a solution of 2% sodium chloride and 3% acetic acid by weight in deionized water. An additional simulant, 2% sodium chloride in deionized water, is processed for 90 minutes at 121° C. and 1.05 kg/cm². Adhesion tests are performed as described above. Blush and corrosion are rated visually.

Example 1

Reaction of methyl 4-hydroxyphenylacetate with 1,10-decanediamine

In a series of runs, methyl 4-hydroxyphenylacetate (CAS No. 14199-15-6) and 1,10-decanediamine (CAS No. 646-25-3) were heated in xylene under reflux at a 2:1.1 ester: diamine molar ratio at 143° C. for 24 hours and in the presence or absence of various catalysts as further described below in Table 1:

TABLE 1

| Run No. | Catalyst | Yield, wt. % |
| --- | --- | --- |
| 1-1 | None | 56 |
| 1-2 | 10 wt. % titanium isopropoxide (Ti(OiPr)$_4$ | 91 (85% after purification) |

TABLE 1-continued

| Run No. | Catalyst | Yield, wt. % |
|---|---|---|
| 1-3 | 10 wt. % TYZOR™ PC 64 | 94 |
| 1-4 | 10 wt. % TYZOR AC 422 | 57 |

The product, a yellow to brown solid, precipitated during the reaction and was easily purified by washing with chloroform. The unreacted raw materials and catalyst mainly remained in the solvent phase. The product yields and structure were determined using proton NMR analysis. The NMR spectrum for the purified product of Run No. 1-3 in Table 1 is shown in FIG. 1, with the suspected peaks for the small remaining quantities of the unreacted raw materials being encircled at a chemical shift of about 3.6 ppm. The product, a para-cresol-terminated diamide, had a purity of 97.5 wt. % by NMR and is shown below in Formula IA:

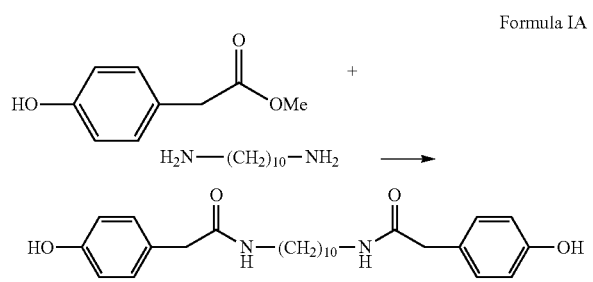

Formula IA

Formula IA is a version of Formula I in which x and y are 1, m and n are 1, $R^1$ and $R^5$ are hydrogen and $R^3$ is the decylene radical —$(CH_2)_{10}$—.

Use and selection of an appropriate catalyst, selection of an appropriate solvent and selection of appropriate reaction conditions generally will affect product yield. For example, when the reaction was repeated using no catalyst, HYDROSOL A170 (B.P. 140-200° C.) from DHC SolventChemie GmbH as the solvent and a heating temperature and time of 153° C. for 24 hours, no product was obtained.

Example 2

Reaction of methyl 4-hydroxyphenylacetate with an aliphatic polyetherdiamine

Using the method of Example 1, methyl 4-hydroxyphenylacetate and JEFFAMINE EDR 176 polyetherdiamine (available from Huntsman Corporation) were heated in xylene or in HYDROSOL A170 solvent under reflux at a 2:1 ester:diamine molar ratio in the presence or absence of titanium isopropoxide catalyst as further described below in Table 2:

TABLE 2

| Run No. | Catalyst | Solvent | Heating Conditions | Yield, wt. % |
|---|---|---|---|---|
| 2-1 | None | Xylene | 143° C., 24 h | 68 |
| 2-2 | None | HYDROSOL A170 | 153° C., 24 h | ~32 |
| 2-3 | 10 wt. % titanium isopropoxide (Ti(OiPr)$_4$ | Xylene | 143° C., 24 h | 87 |
| 2-4 | 10 wt. % titanium isopropoxide (Ti(OiPr)$_4$ (fresh catalyst) | Xylene | 143° C., 24 h | 92 |

Figure 2:
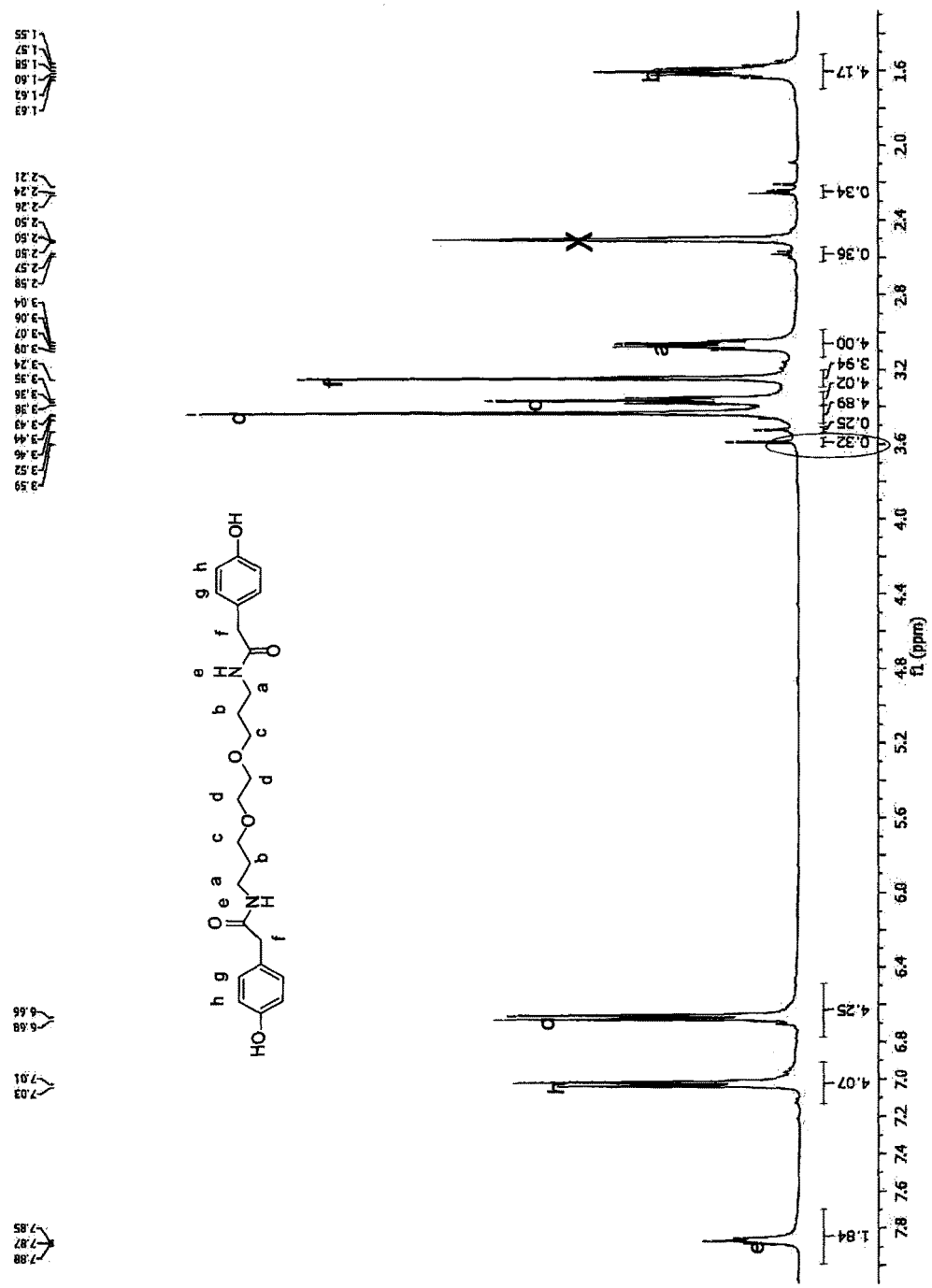

The NMR spectrum for the purified product of Run No. 2-4 in Table 2 is shown in FIG. 2, with the suspected peaks for the small remaining quantities of the unreacted raw materials being encircled at a chemical shift of about 3.6 ppm. The product, a para-cresol-terminated diamide, had a purity of 90 wt. % by NMR and is shown below in Formula IB:

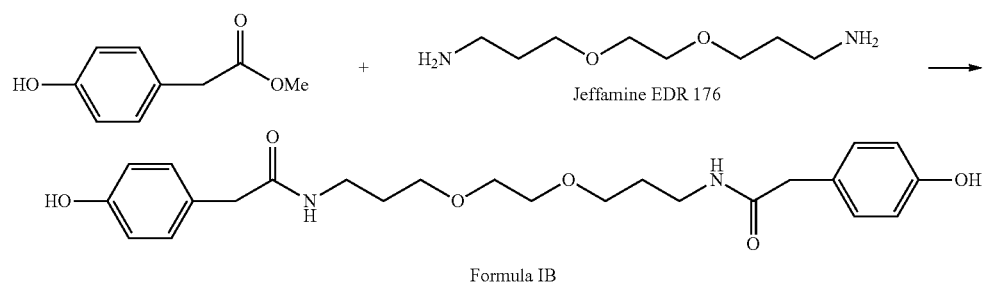

Formula IB

Formula IB is a version of Formula I in which x and y are 1, m and n are 1, $R^1$ and $R^5$ are hydrogen and $R^3$ is the radical —$(CH_2)_3O(CH_2)_2O(CH_2)_3$—.

Example 3

Reaction of methyl 4-hydroxyphenylacetate with an aliphatic branched diamine

Using the method of Example 1, methyl 4-hydroxyphenylacetate and PRIAMIN 1074 aliphatic ($C_{36}$) branched diamine (available from Croda International) were heated in xylene or in HYDROSOL A170 solvent under reflux at a 2:1 ester:diamine molar ratio in the presence or absence of titanium isopropoxide catalyst as further described below in Table 3:

TABLE 3

| Run No. | Catalyst | Solvent | Heating Conditions | Yield, wt. % |
|---|---|---|---|---|
| 3-1 | None | HYDROSOL A170 | 153° C., 24 h | — |
| 3-2 | 10 wt. % titanium isopropoxide (Ti(OiPr)$_4$ (fresh catalyst) | Xylene | 143° C., 24 h | 51 |

The product did not precipitate, and a homogeneous reaction mixture was obtained in Run No. 3-2. However, because PRIAMIN 1074 is soluble in pentane, washing with pentane could be used to purify the di(amido(alkyl)phenol) product.

Example 3

Reaction of 4-(2-aminoethyl)phenol with an aliphatic dimethyl ester

In two runs, 4-(2-aminoethyl)phenol (CAS No. 51-67-2) and decanedioic acid dimethyl ester (CAS No. 106-79-6) were heated in xylene under reflux at a 2:1 amine:diester molar ratio at 143° C. for 24 hours and in the presence or absence of titanium isopropoxide catalyst as further described below in Table 4:

TABLE 4

| Run No. | Catalyst | Yield, wt. % |
|---|---|---|
| 4-1 | None | 12 |
| 4-2 | 10 wt. % titanium isopropoxide (Ti(OiPr)$_4$ (fresh catalyst) | 15 |

Example 5

Reaction of 1,5-diamino-2-methylpentane with m-hydroxybenzoic acid

Figure 3:
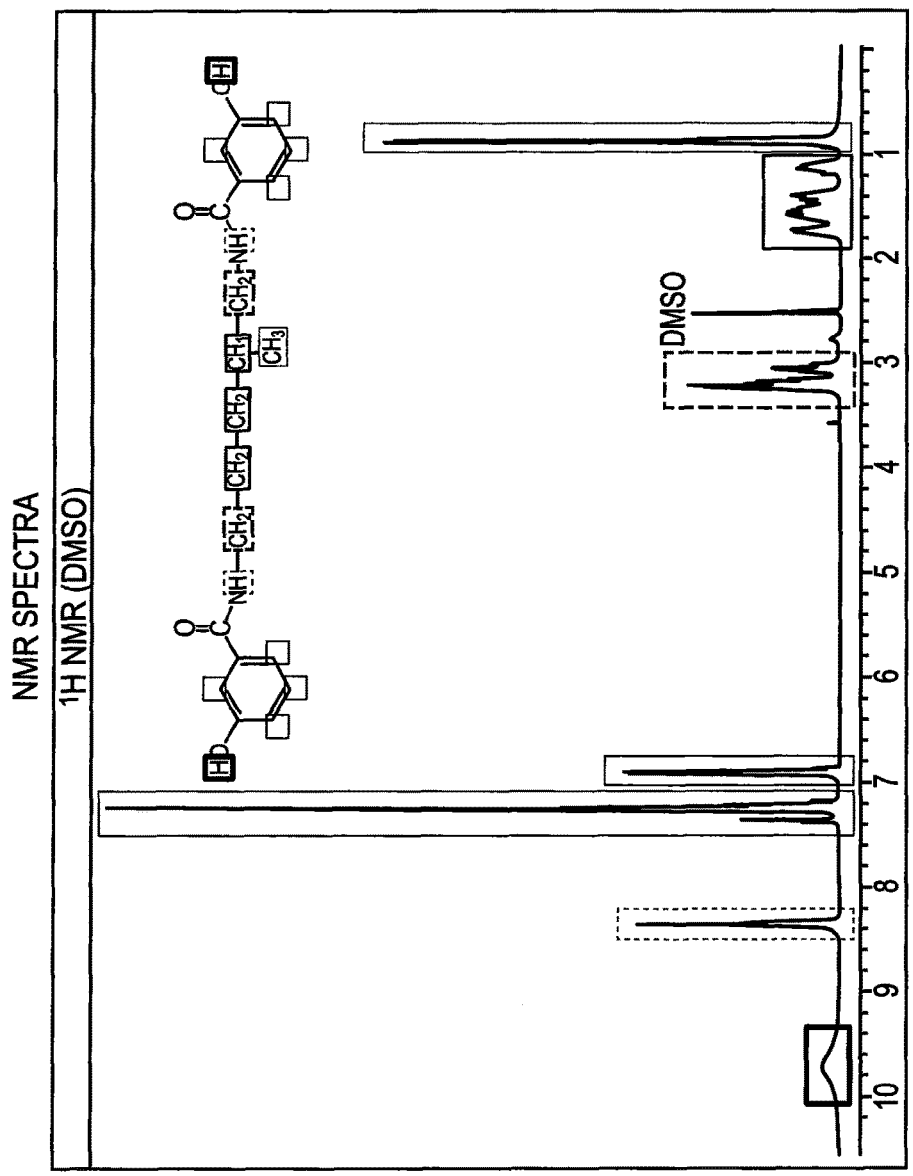

In a glass vessel equipped with a total condenser, stirrer, temperature regulation and a nitrogen atmosphere, 30 parts 1,5-diamino-2-methylpentane (DYTEK™ A amine from Invista, also known as 2-methylpentaneethylenediamine) was heated at 150° C. Under agitation, 81.1 parts m-hydroxybenzoic acid were added slowly and dissolved in the diamine. The temperature was progressively increased to 210° C. and maintained there for 15 minutes. Next, vacuum was progressively applied (from 10 to 1 mBar) in order to eliminate water and unreacted monomers. The progress of the reaction was followed using proton NMR analysis. When the specific signals of amines disappeared after about 3 hours, the product was cooled. The reaction yield was 95% calculated based on the initial raw materials. The NMR spectrum for the product is shown in FIG. 3. The product may be diluted in solvent if desired, for example in a 60:40 mixture of SOLVESSO™ 100 aromatic fluid (from Exxon-Mobil Chemical) and 2-butoxyethanol.

Example 6

Polymer Based on Hindered Diglycidyl Ether and Di(Amido(Alkyl)Phenol)

An upgraded molecular weight polymer was prepared from a diglycidyl ether of 4,4'-methylenebis(2,6-dimethylphenol) and the above-described di(amido(alkyl)phenol) of Example 2, Run No. 2-3 using the ingredients shown below in Table 5:

TABLE 5

| Ingredient | Amount, parts |
|---|---|
| Diglycidyl ether of 4,4'-methylenebis(2,6-dimethylphenol) | 30.5 |
| Dimethyl sulfoxide (DMSO) | 7.6 |
| Di(amido(alkyl)phenol) of Example 2, Run No. 2-3 | 30.0 |
| DMSO | 12.9 |
| DMSO | 40.0 |
| Total | 121.0 |

The diglycidyl ether and first DMSO charge were combined in a 250 mL reaction vessel closed with a flat flange lid equipped with 5 ground necks respectively fitted with a working temperature sensor, nitrogen inlet, stirrer, condenser and stopper. Using an electric heating mantle, the flask contents were heated to 120° C. under stirring and a stream of bubbled nitrogen. Next a premix containing the di(amido(alkyl)phenol) and second DMSO charge were added using a dropping funnel over 30 minutes at 120° C. The temperature was maintained between 118 and 123° C. until a weight per epoxide value of about 2200-2800 grams was obtained. The product was thinned by adding the final DMSO charge at 120° C.

Example 7

Coating Compositions

A 52.6 wt. % non-volatile compounds (NVC) solution of the Example 6 polymer was used as a binder in coating compositions containing the conventional additional ingredients shown below in Table 6:

TABLE 6

Coating Compositions

| | Amount, parts | |
|---|---|---|
| Ingredient | Run No. 6-1 | Run No. 6-2 |
| Example 6 polymer (52.6% NVC) | 68.2 | 68.2 |
| Resole-type phenolic resin (phenol + para-t-butyl phenol, 60% NVC) | 11.35 | 0 |
| Resole-type phenolic resin (phenol, 60% NVC) | 0 | 8 |
| Resole-type phenolic resin (para-t-butyl phenol, 60% NVC) | 0 | 15 |
| Mixture 0.5 parts 10% H$_3$PO$_4$ in dipropylene glycol methyl ether, 9 parts xylene and 4 parts n-butanol | 20.5 | 20.5 |
| 1:1 Mixture xylene:n-butanol | 2 | 3 |
| Wax, 18% NVC | 2 | 2 |
| Total | 104.05 | 116.7 |

The coating compositions were applied on electrolytic tin plate substrates (2.8/2.8 g/m$^2$ tin coating weight) at a dry film weight of about 6-8 g/m$^2$ and cured in a ventilated oven for about 10-12 minutes total oven time until a peak metal temperature of 200° C. was reached. After cooling and ageing the coated panels for 12 hours, the coatings were evaluated and found to have the performance results shown below in Table 7:

TABLE 7

| Coating Performance | | |
|---|---|---|
| Evaluation | Run No. 6-1 | Run No. 6-2 |
| Wedge bend, % | 90% | 89% |
| Porosity before retort | 31 | 27 |
| Porosity after retort in water | 46 | 48 |
| Porosity after retort in 3% aqueous acetic acid | 44 (slight blush) | 44 (slight blush) |
| Porosity after retort in 1% salt solution | 50 | 30 |

The wedge bend results were excellent or good. The coatings were somewhat more porous than might have been obtained using a higher coating weight or a more optimized formulation. However, the results in Table 7 show a relatively limited increase in porosity following exposure to water, acid and salt solutions.

Having thus described preferred embodiments of the disclosed compounds, compositions and methods, those of skill in the art will readily appreciate that the teachings found herein may be applied to yet other embodiments within the scope of the claims hereto attached. The complete disclosure of all listed patents, patent documents and publications (including material safety data sheets, technical data sheets and product brochures for the raw materials and ingredients used in the Examples) are incorporated herein by reference as if individually incorporated.

We claim:

1. An article comprising:
a. a food or beverage packaging container, or portion thereof, having a food or beverage contact surface comprising a metal substrate; and
b. a coating formed from a coating composition disposed in powdered form on the food or beverage contact surface;
the coating composition comprising a polymer made from an α, Ω telechelic di(amido(alkyl)phenol) and a material that reacts with hydroxyl groups on phenol rings, and being substantially free of bisphenol A and bisphenol F, and wherein the polymer is a polyester, polyurethane, polycarbonate or phenolic resin.

2. The article according to claim 1, wherein the material that reacts with hydroxyl groups on phenol rings is an epoxide.

3. The article according claim 2, wherein the material that reacts with hydroxyl groups on phenol rings is epichlorohydrin.

4. The article according to claim 2, wherein the epoxide is a diepoxide and the polymer includes —$CH_2$—CH(OH)—$CH_2$— or —$CH_2$—$CH_2$—CH(OH)— segments.

5. The article according to claim 1, wherein the polymer is an epoxy-terminated or phenoxy-terminated polyether.

6. The article according to claim 1, wherein the polymer has air oxidizable unsaturated groups.

7. The article according to claim 1, wherein the polymer is free radically curable.

8. The article according to claim 1, wherein the coating composition further comprises a lubricant that facilitates manufacture of fabricated metal articles by imparting lubricity to the coated metal substrate, a pigment, a curing agent and a catalyst to increase the rate of cure.

9. The article according to claim 1, wherein the food or beverage packaging container comprises a two-piece drawn food can, a three-piece food can, a food can end, a drawn and ironed food or beverage can, a beverage can end, an easy open can end, or a twist-off closure lid.

10. An article comprising:
a. a food or beverage packaging container, or portion thereof, having a food or beverage contact surface comprising a metal substrate; and
b. a coating formed from a coating composition disposed in liquid or powdered form on the food or beverage contact surface;
the coating composition comprising a polymer made from a polyphenol and a material that reacts with hydroxyl groups on phenol rings, and wherein the polyphenol has the formula:

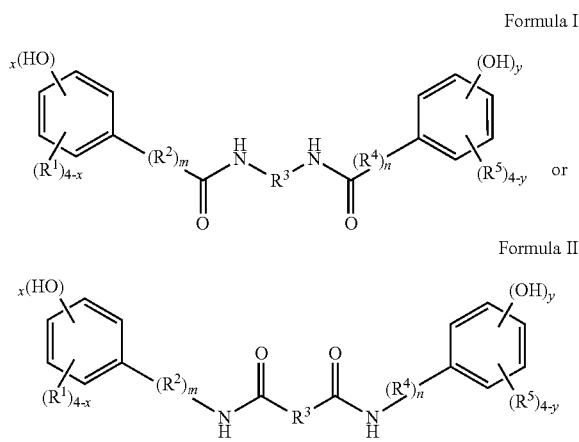

Formula I

Formula II wherein:
x and y may be the same or different, and are each an integer from 1 to 3;
m and n may be the same or different, and are 0 or 1;
$R^1$ and $R^5$ may be the same or different and independently are monovalent atoms or monovalent organic groups which may contain heteroatoms;
$R^2$ and $R^4$ may be the same or different and when present independently are divalent linear aliphatic organic groups containing 1 to 12 carbon atoms and may contain heteroatoms; and
$R^3$ is a divalent organic group that may contain heteroatoms.

11. The article according to claim 10, wherein the polyphenol has Formula I.

12. The article according to claim 10, wherein the polyphenol has Formula II.

13. The article according to claim 10, wherein x and y are 1 and $R^1$ and $R^5$ are hydrogen.

14. The article according to claim 10, wherein $R^3$ is a divalent linear aliphatic group.

15. The article according to claim 10, wherein the polymer is made from a para-cresol-terminated diamide of Formula I having the formula:

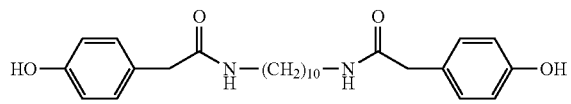

in which x and y in Formula I are 1, m and n are 1, $R^1$ and $R^5$ are hydrogen and $R^3$ is the decylene radical —$(CH_2)_{10}$—, or wherein the polymer is made from a para-cresol-terminated diamide of Formula I having the formula:

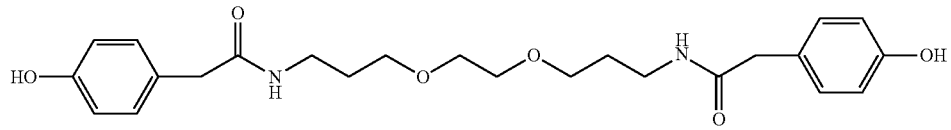

in which x and y in Formula I are 1, m and n are 1, $R^1$ and $R^5$ are hydrogen and $R^3$ is the radical —$(CH_2)_3O(CH_2)_2 O(CH_2)_3$—.

16. The article according to claim 10, wherein the coating composition further comprises a lubricant that facilitates manufacture of fabricated metal articles by imparting lubricity to the coated metal substrate, a pigment, a curing agent and a catalyst to increase the rate of cure.

17. The article according to claim 10, wherein the food or beverage packaging container comprises a two-piece drawn food can, a three-piece food can, a food can end, a drawn and ironed food or beverage can, a beverage can end, an easy open can end, or twist-off closure lid.

18. The article according to claim 10, wherein the coating composition comprises the polymer in the liquid carrier, and wherein the liquid carrier comprises one or more organic solvents.

19. The article according to claim 10, wherein the coating composition comprises the polymer in the liquid carrier, and wherein the liquid carrier comprises water.

20. The article according to claim 10, wherein the coating composition is in powdered form.

21. The article according to claim 10, wherein the coating composition is substantially free of bisphenol A and bisphenol F.

22. A method for making a coated food or beverage packaging container, the method comprising:
applying to a food or beverage contact surface of a metal substrate a liquid or powdered coating composition comprising a polymer made from a polyphenol and a material that reacts with hydroxyl groups on phenol rings, wherein the polyphenol has the formula:

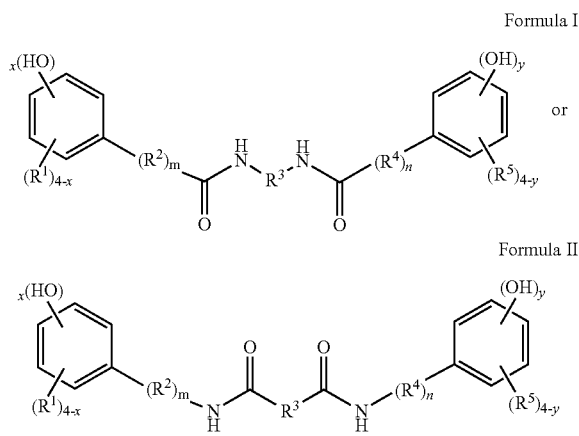

wherein:
x and y may be the same or different, and are each an integer from 1 to 3;
m and n may be the same or different, and are 0 or 1;
$R^1$ and $R^5$ may be the same or different and independently are monovalent atoms or monovalent organic groups which may contain heteroatoms;
$R^2$ and $R^4$ may be the same or different and when present independently are divalent linear aliphatic organic groups containing 1 to 12 carbon atoms and may contain heteroatoms; and
$R^3$ is a divalent organic group that may contain heteroatoms;
hardening the composition; and
forming the metal substrate into a food or beverage packaging container or portion thereof prior to or after applying the coating composition to the metal substrate.

\* \* \* \* \*